United States Patent
Zhang et al.

(10) Patent No.: US 10,300,026 B2
(45) Date of Patent: May 28, 2019

(54) USE OF DIHYDROXYACETONE IN PREPARATION OF ANTI-CANCER MEDICAMENTS

(71) Applicants: Shanxi Yabao Health Products Co., Ltd., Yuncheng (CN); Yabao Pharmaceutical Group Co., Ltd., Yuncheng (CN)

(72) Inventors: Jianguo Zhang, Yuncheng (CN); Wuxian Ren, Yuncheng (CN); Peng Wang, Yuncheng (CN); Bangqin Ya, Yuncheng (CN)

(73) Assignees: Shanxi Yabao Health Products Co., Ltd., Yuncheng (CN); Yabao Pharmaceutical Group Co., Ltd., Yuncheng (CN)

( * ) Notice: Subject to any disclaimer, the term of this patent is extended or adjusted under 35 U.S.C. 154(b) by 0 days.

(21) Appl. No.: 15/750,726

(22) PCT Filed: May 26, 2016

(86) PCT No.: PCT/CN2016/083466
§ 371 (c)(1),
(2) Date: Feb. 6, 2018

(87) PCT Pub. No.: WO2017/032111
PCT Pub. Date: Mar. 2, 2017

(65) Prior Publication Data
US 2019/0000777 A1    Jan. 3, 2019

(30) Foreign Application Priority Data

Aug. 24, 2015  (CN) .......................... 2015 1 0523222
Dec. 1, 2015    (CN) .......................... 2015 1 0867079
Dec. 1, 2015    (CN) .......................... 2015 1 0867132

(51) Int. Cl.
| | | |
|---|---|---|
| *A61K 31/121* | (2006.01) | |
| *A61K 9/02* | (2006.01) | |
| *A61K 9/08* | (2006.01) | |
| *A61K 33/24* | (2019.01) | |
| *A61K 45/06* | (2006.01) | |
| *A61K 9/00* | (2006.01) | |
| *A61K 9/16* | (2006.01) | |
| *A61K 9/20* | (2006.01) | |
| *A61K 9/48* | (2006.01) | |
| *A61P 35/00* | (2006.01) | |

(52) U.S. Cl.
CPC .......... *A61K 31/121* (2013.01); *A61K 9/0019* (2013.01); *A61K 9/0053* (2013.01); *A61K 9/02* (2013.01); *A61K 9/08* (2013.01); *A61K 9/1641* (2013.01); *A61K 9/1652* (2013.01); *A61K 9/2054* (2013.01); *A61K 9/2059* (2013.01); *A61K 9/4858* (2013.01); *A61K 9/4866* (2013.01); *A61K 33/24* (2013.01); *A61K 45/06* (2013.01); *A61P 35/00* (2018.01)

(58) Field of Classification Search
CPC .. A61K 31/121; A61K 9/0019; A61K 9/0053; A61K 9/02; A61K 9/08; A61K 9/1641; A61K 9/1652; A61K 9/2054; A61K 9/2059; A61K 9/4866; A61K 33/24; A61K 45/06
USPC ......................................... 424/649
See application file for complete search history.

(56) References Cited

FOREIGN PATENT DOCUMENTS

| | | |
|---|---|---|
| CN | 1679526 | 10/2005 |
| CN | 101690820 | 4/2010 |
| JP | 2012-508173 | 4/2012 |

OTHER PUBLICATIONS

International Search Report issued in International Application No. PCT/CN2016/083466, dated Aug. 31, 2016.
Petersen et al., "Sunless skin tanning with dihydroxyacetone delays broad-spectrum ultraviolet photocarcinogenesis in hairless mice," *Mutation Research*, 542: 129-138 (2003).
Li et al., "Observation of clinical effect of 5% dihydroxyacetone cream for external use on 46 vitiligo patients" Railway Central Hospital of Hubei Xiangfan, Dermatology Department, Oct. 27, 2003.
Office Action issued in Corresponding Japanese Patent Application No. 2018-503509, dated Oct. 26, 2018. (Machine Translation).

*Primary Examiner* — Yevgeny Valenrod
(74) *Attorney, Agent, or Firm* — Norton Rose Fulbright US LLP

(57) ABSTRACT

Provided is a use of dihydroxyacetone in the preparation of a medicament, the medicament being used for treating a cancer.

16 Claims, 3 Drawing Sheets

USE OF DIHYDROXYACETONE IN PREPARATION OF ANTI-CANCER MEDICAMENTS

CROSS-REFERENCE TO RELATED APPLICATIONS

This application is a national phase under 35 U.S.C. § 371 of International Application No. PCT/CN2016/083466, filed May 26, 2016, which claims priority to Chinese Patent Application No. 201510523222.6 filed Aug. 24, 2015, Chinese Patent Application No. 201510867132.9, filed Dec. 1, 2015, and Chinese Patent Application No. 201510867079.2, filed Dec. 1, 2015, the contents of which are incorporated herein by reference in their entireties, and used for all purposes specifically and completely set forth herein.

TECHNICAL FIELD

The present invention belongs to the pharmaceutical field, and in particular relates to a novel use of a compound, in particular to use in the preparation of anti-cancer medicaments.

BACKGROUND 1,3-dihydroxyacetone or dihydroxyacetone, abbreviated as DHA, is the simplest ketose with three carbon atoms. It appears white or off-white powdery crystal form. It tastes sweet and cool, and is inclined to absorb moisture and decompose. The normal form is a crystalline dimer (1,4-Dioxane), which is slowly dissolved in 1 part of water or 15 parts of ethanol, and slightly soluble in diethyl ether. However, it reverts to the monomer via dissolution or heating. The monomer is very soluble in water and organic solvents such as ethanol, acetone and diethyl ether and the like. It has a melting point of 75-80° C., a water solubility of more than 250 g·$L^{-1}$ (at 20° C.), and is stable at pH 6.0. 1,3-dihydroxyacetone is an important raw material for chemical industry and biochemistry, a synthetic intermediate for medicine and pesticide, and a food additive with multiple functions. It has a very wide range of applications.

Dihydroxyacetone has moisturizing, sunscreen and anti-ultraviolet radiation effects, and can prevent the skin moisture from evaporating excessively. Thus, it can be used as formula ingredients in cosmetics and has a special effect when particularly used as sunscreen cream. Dihydroxyacetone is an intermediate product of glycometabolism, playing an important role in the process of glycometabolism. It has an effect of reducing body fat of pig and thus can improve lean meat rate. Supplementation of dihydroxyacetone can increase body's metabolic rate and enhance the oxidation of fatty acid, and potentially fat can be consumed efficiently so as to reduce body fat. Therefore, dihydroxyacetone can exhibit an effect of anti-obesity and reduce an incidence of related diseases. It can also improve the insulin sensitivity and reduce the plasma cholesterol level caused by high cholesterol diet. The long term supplementation of dihydroxyacetone can increase blood glucose utilization rate and thus save muscle glycogen, which can improve aerobic endurance performance for athletes.

Although dihydroxyacetone (DHA) is widely applied, there is no report on its anti-cancer effect when used alone or in combination.

Cisplatin, the chemical name of which is cis-diammine platinum dichloride, is a cell cycle non-specific medicament with cytotoxicity. It can inhibit the DNA replication process of cancer cells, and damage the structure on cancer cell membrane, thus having a strong broad-spectrum anti-cancer effect. However, it has serious side effects including bone marrow transplantation, leukopenia, strong gastrointestinal reactions, nausea, vomiting, diarrhea, irreversible renal toxicity and renal failure, neurotoxicity, allergic reactions, and electrolyte imbalance in the clinic. Although cisplatin has such a highly toxicity, it is still a first-line medicine in clinical treatment for solid tumors due to its exact broad-spectrum anti-cancer effect.

However, it is impossible to improve curative effect by increasing the dosage of cisplatin. Therefore, a therapeutic regimen in combination with cisplatin, which can significantly enhance the anti-cancer effect without increasing toxicity, is always an important subject of cancer medical research.

SUMMARY OF THE INVENTION

The present invention is intended to address one of technical problems in the related art at least to a certain extent.

The present invention relates to a novel use of dihydroxyacetone.

Said novel use of the present invention mainly includes use of dihydroxyacetone in the preparation of anti-cancer medicaments. The present invention provides a novel use of dihydroxyacetone, which exhibits a better activity against a variety of cancers. In addition, dihydroxyacetone is already widely used in the human body, and is a chemical substance with high safety. Therefore, the novel use provided in the present invention allows this substance to expand its application to human body, which is expected to be applied much more in the field of healthcare food, medicine, etc.

The cancers that can be treated by dihydroxyacetone according to the present invention are not particularly specified. The examples thereof include malignant melanoma, malignant lymphoma, digestive organ cancer, lung cancer, esophageal cancer, gastric cancer, colorectal cancer, rectal cancer, colon cancer, ureteral cancer, gallbladder carcinoma, biliary tract cancer, mastocarcinoma, liver cancer, pancreatic cancer, testicular cancer, mandible cancer, tongue cancer, lip carcinoma, oral cancer, laryngeal cancer, larynx cancer, ovarian cancer, uterine cancer, prostate cancer, thyroid cancer, brain cancer, sarcoma, hemangioma, leukemia, polycythemia vera, neuroblastoma, retinoblastoma, myeloma, bladder cancer, osteosarcoma, myosarcoma, skin cancer, basal cell carcinoma, skin affiliated organ cancer, skin metastatic cancer, skin melanoma and the like.

According to a specific embodiment of the present invention, the cancer can be a nervous system cancer, including but not limited to neuroblastoma and glioma.

According to a specific embodiment of the present invention, the cancer can be a digestive system cancer, including but not limited to colon cancer, rectal cancer, liver cancer, gastric cancer, and pancreatic cancer.

According to a specific embodiment of the present invention, the cancer can be a reproductive system cancer and a urinary system cancer, including but not limited to cervical cancer, breast cancer, ovarian cancer, prostate cancer, and bladder cancer.

According to a specific embodiment of the present invention, the cancer can be a skin cancer, a bone cancer and a joint system cancer, including but not limited to melanoma, epidermal squamous cell carcinoma, rhabdomyoma, multiple myeloma, and sarcoma.

According to a specific embodiment of the present invention, the cancer can be a respiratory system cancer, including but not limited to lung cancer, throat cancer, and oral cancer.

According to a specific embodiment of the present invention, the cancer can be a hematologic cancer and a gland cancer, including but not limited to leukemia, lymphoma, and thyroid cancer.

According to an aspect of the present invention, the present invention provides use of dihydroxyacetone in the preparation of medicaments for treating cancers.

According to some embodiments of the present invention, said cancers comprise at least one selected from the group consisting of nervous system cancer, digestive system cancer, reproductive system cancer, urological system cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to another aspect of the present invention, the present invention provides use of dihydroxyacetone for treating cancers.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a method of treating cancers, comprising administering dihydroxyacetone to a patient.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a pharmaceutical composition for anti-cancer comprising dihydroxyacetone as an active ingredient.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

The present invention provides a pharmaceutical combination of dihydroxyacetone and cisplatin in anti-cancer applications.

According to yet another aspect of the present invention, the present invention provides a pharmaceutical composition for treating cancer comprising dihydroxyacetone and cisplatin as active ingredients. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a pharmaceutical combination for treating cancer consisting of dihydroxyacetone and cisplatin. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to a specific embodiment of the present invention, the dihydroxyacetone in the pharmaceutical combination can be in the form of an oral preparation, and cisplatin can be in the form of an injection.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides use of dihydroxyacetone in the preparation of medicaments for treating cancers, wherein dihydroxyacetone and cisplatin are administered simultaneously to a subject. The modes of administration can be in accordance with their conventional route, dosage and frequency of administration, respectively.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides use of dihydroxyacetone for treating cancers, wherein dihydroxyacetone and cisplatin are administered simultaneously to a subject. The modes of administration can be in accordance with their conventional route, dosage and frequency of administration, respectively.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a method of treating cancers comprising administering dihydroxyacetone to a patient, wherein dihydroxyacetone and cisplatin are administered simultaneously to a subject. The modes of administration can be in accordance with their conventional route, dosage and frequency of administration, respectively.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides use of a combination of dihydroxyacetone and cisplatin in the preparation of medicaments for treating cancers. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides use of a combination of dihydroxyacetone and cisplatin for treating cancers. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a method of treating cancers, comprising administering a combination of dihydroxyacetone and cisplatin to a patient. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides a kit for treating cancer, wherein it comprises dihydroxyacetone and cisplatin. Dihydroxyacetone and cisplatin have a synergistic effect on the treatment of cancers. The pharmaceutical combination of dihydroxyacetone and cisplatin can produce a significantly better effect than dihydroxyacetone or cisplatin used alone. Meanwhile, dihydroxyacetone does not increase the toxic and side effects of cisplatin.

According to a specific embodiment of the present invention, dihydroxyacetone and cisplatin in the kit are provided in different containers.

According to a specific embodiment of the present invention, dihydroxyacetone is in the form of an oral preparation, and cisplatin is in the form of an injection.

According to a specific embodiment of the present invention, dihydroxyacetone and cisplatin in the kit are provided in a weight ratio of (3375-4125):1. Preferably, dihydroxyacetone and cisplatin are provided in a weight ratio of 3750:1.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

According to yet another aspect of the present invention, the present invention provides use of a combination of dihydroxyacetone and cisplatin in the preparation of a kit for treating cancers.

According to some embodiments of the present invention, said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

According to a specific embodiment of the present invention, said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer and bladder cancer, melanoma, epidermal squamous cell carcinoma, rhabdomyoma, multiple myeloma, sarcoma, lung cancer, throat cancer, oral cancer, leukemia, lymphoma and thyroid cancer.

The applications provided in the present invention include not only the applications in malignancies, but also ones in benign cancers.

According to a specific embodiment of the present invention, dihydroxyacetone can be used to inhibit cancer metastasis, and is particularly useful as a postoperative cancer metastasis inhibitor.

It should be noted that the term "dihydroxyacetone" used herein should be broadly understood to include dihydroxyacetone in monomeric form and also cover the normal forms of dihydroxyacetone, such as various crystalline forms, dimer or multimer, hydrate and the like.

According to some embodiments of the present invention, dihydroxyacetone can be a monomer, a dimer or a multimer.

In the application of the present invention, dihydroxyacetone can be administered to human or animals orally, via intravenous injection, intramuscular injection, subcutaneous or intradermal injection, rectally, or mucosally. The examples of oral preparations can be tablets, pills, granules, powders, capsules, oral solutions, suspensions, emulsions, syrups and the like. The non-oral preparations can be transdermal preparations, for example injections, drops, nasal drops, inhalants, suppositories, ointments, creams, powder coating preparations, or patches. In the applications of the present invention, dihydroxyacetone can be embedded into pills and sustained-release preparations prepared from well-known techniques can be used.

Said medicament of the present invention is suitably applied in the form of pharmaceutical compositions. Such compositions can be mixed with one or more pharmaceutically acceptable carriers or excipients in a conventional manner. If possible, dihydroxyacetone is administered as an active pharmaceutical ingredient in the therapy.

As needed, the pharmaceutically acceptable carriers can be added to the pharmaceutical composition of the present invention to prepare a pharmaceutical preparation. Dihydroxyacetone is used as the primary medicament or one of the primary medicaments.

The pharmaceutical composition of the present invention can contain pharmaceutically acceptable carriers, as needed. Dihydroxyacetone as the pharmaceutically active ingredient represents 0.01 to 99.99% by weight percentage in the formulation and the balance is a pharmaceutically acceptable carrier. The pharmaceutical formulation of the present invention is present in unit dosage form. Said unit dosage form means the unit of formulation, such as one tablet, one capsule, one bottle in oral solutions, one bag in granules, or one injection.

According to the pharmaceutical compositions of the present invention, the formulation via oral administration can contain conventional excipients such as binders, fillers, diluents, agents for tablets, lubricants, disintegrants, colorants, flavoring agents and humectants. If necessary, the tablets can be coated.

Suitable fillers comprise cellulose, mannitol, lactose and the like. Suitable disintegrants include starch, polyvinylpyrrolidone and starch derivatives such as sodium starch glycolate. Suitable lubricants include, for example, magnesium stearate. Suitable pharmaceutically acceptable humectants include sodium dodecyl sulfate.

Solid oral compositions can be prepared by conventional methods such as mixing, filling, tableting and the like. The active substances can be distributed throughout those compositions contained a large amount of filler by repeated mixing.

The oral liquid formulations can be in the form of, for example, aqueous or oily suspensions, solutions, emulsions, syrups or elixirs, or can be a dry product that can be compounded with water or other suitable carriers prior to use. Such liquid formulations can contain conventional additives, for example, suspending agents such as sorbitol, syrup, methylcellulose, gelatin, hydroxyethylcellulose, carboxymethylcellulose, aluminum stearate gel or hydrogenated edible fat; emulsifying agents such as lecithin, sorbitan monooleate or acacia; nonaqueous carriers (which can include edible oils) such as almond oil, fractionated coconut oil, oily esters such as glycerol esters, propylene glycol or ethanol; preservative such as paraben or propylparaben or sorbic acid. If necessary, a conventional flavoring or coloring agent can be included.

For injections, liquid unit dosage form prepared comprises the active substance of the present invention and the sterile carrier. Depending on the carrier and concentration, the compound can be suspended or dissolved. Generally, the solution can be prepared by dissolving the active substance into a carrier, filtering and sterilizing, dispensing into a suitable vial or ampoule, and then sealing. An adjuvant such as a local anesthetic, a preservative and a buffer can be also dissolved in such a carrier. In order to improve stability, the composition can be frozen after dispensing into a vial and removed of water under vacuum.

Optionally, suitable pharmaceutically acceptable carriers can be added to the pharmaceutical composition of the present invention when being prepared into a medicament. The pharmaceutically acceptable carrier is selected from the group consisting of mannitol, sorbitol, sodium pyrosulfite, sodium bisulfite, sodium thiosulfate, cysteine hydrochloride, thioglycolic acid, methionine, vitamin C, EDTA disodium, EDTA calcium sodium, monovalent alkali metal carbonates, acetates, phosphates or aqueous solutions thereof, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivatives, cellulose and its derivatives, alginate, gelatin, polyvinylpyrrolidone, glycerin, tween 80, agar, calcium carbonate, calcium bicarbonate, surfactants, polyethylene glycol, cyclodextrin, β-cyclodextrin, phospholipids, kaolin, talc, calcium stearate, magnesium stearate, and the like.

DESCRIPTION OF THE DRAWINGS

The foregoing and/or additional aspects and advantages of the present invention will become apparent and be readily understood from the following description of the examples taken in conjunction with the accompanying drawings, in which.

DETAILED DESCRIPTION OF THE INVENTION

Figure 1:
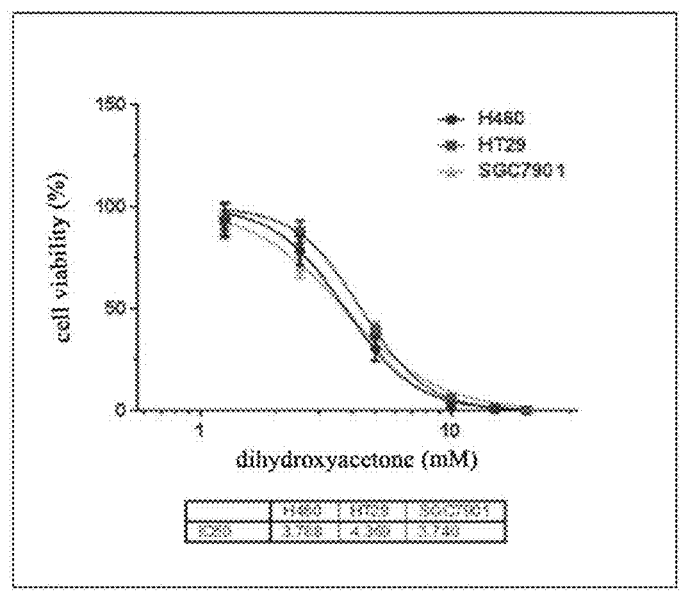
FIG. 1 is the IC50 statistical graph of dihydroxyacetone for H460, HT29, and SGC7901 cell lines according to Example 1 of the present invention.

Examples of the present invention are described in detail below. Said examples are shown in the accompanying drawings, wherein the same or similar reference numbers always refer to the same or similar elements or elements having the same or similar functions. The examples described below with reference to the accompanying drawings are exemplary, only for the purpose of explaining the present invention, and cannot be construed as limiting the present invention.

EXAMPLES

Example 1

The use of dihydroxyacetone for preparing a medicament in the present invention is demonstrated by the following experiments:

1. Experimental Method 1.1 Materials and Equipments 1.1.1 Reagents

| Name | Item number | Manufacturer |
|---|---|---|
| Leibovitz's L-15 | 11415-064 | Gibco |
| DMEM | 11965-092 | Gibco |
| RPMI 1640 | 11875-093 | Gibco |
| DMEM/F-12 | 11320-033 | Gibco |
| MEM | 11095-080 | Gibco |
| Ham's F-12K | 21127-022 | Gibco |
| McCoy's 5a | 16600-082 | Gibco |
| IMDM | 12440-053 | Gibco |
| FBS | 10099-141 | Gibco |
| BCS | 16010-159 | Gibco |
| Penicillin-Streptomycin | 15140-122 | Gibco |
| CellTiter-Glo Luminescent Cell Viability Assay | G7571 | Promega |

1.1.2 Consumables

| Name | Item number/Specification | Brand |
|---|---|---|
| 384-well plate | 3707 | Corning |

1.1.3 Equipments

| Name | Item number/Specification | Brand |
|---|---|---|
| Multichannel Pipettes (8 channels) | 0.5-10 μL | Rainin |
| HTRF reader | | BMG PHERAstar |

1.1.4 Experimental Medicaments 15 g of the commercially available 1,3-dihydroxyacetone in the solid powder form was added into 100 mL of 5% glucose (infusion bottle), then filled into 100 bottles.

Control compound: cisplatin (DDP): Qilu Pharmaceutical Co., Ltd., batch number: 2WA2A1404016A, 20 mg/bottle; 1 mg/ml of stock solution was prepared by using 5% glucose solution, and stored at −20° C.

1.2 Experimental Method 1.2.1 Osmotic Pressure Measurement

The samples were diluted to different concentrations via RPMI-1640 medium, and then the osmotic pressure of the samples was measured by using the freezing point osmometer from LOSER Company of Germany.

1.2.2 Conditions for Cell Culture

| No. | Cell line | Full name | Medium | Conditions for cell culture |
|---|---|---|---|---|
| 01 | WIL2-S | Human B lymphocyte | RPMI 1640 + 10% FBS | 37° C. 95% Air 5% $CO_2$ |
| 02 | BEL-7402 | Human hepatoma cell line | | |
| 03 | HCC1937 | Human breast cancer cell | | |
| 04 | Jurkat (Clone E6-1) | Human T lymphoblastic leukemia cell | | |
| 05 | RPMI-8226 | Multiple myeloma | | |
| 06 | SMMC-7721 | Human hepatoma cell line | | |
| 07 | TF-1α | Human erythroleukemia cell | | |
| 08 | NCI-H460 | Human large cell lung cancer cell line | | |
| 09 | SGC-7901 | Human gastric adenocarcinoma cell | | |
| 10 | Caki-1 | Human renal clear cell carcinoma skin metastatic cell | McCoy's 5a + 10% FBS | |
| 11 | T24 | Human bladder transitional cell carcinoma cell | | |
| 12 | HCT-116 | Human colon cancer cell | | |
| 13 | HT-29 | Human colon cancer cell line | | |
| 14 | A2780 | Human ovarian cancer cell line | MEM + 10% FBS | |
| 15 | DU 145 | Human prostate cancer cell | | |
| 16 | FaDu | Human pharyngeal squamous cell | | |
| 17 | KB | Human oral cancer cell line | | |
| 18 | U87MG | Human spongioblastoma cell line | | |
| 19 | CALU-6 | Human degenerative cancer cell | | |
| 20 | S180 | S180 sarcoma cells | MEM + 10% BCS | |
| 21 | C33A | Human cervical cancer cell | MEM + 10% FBS | |
| 22 | HepG2 | Human hepatoma cell line | | |
| 23 | A375 | Human malignant melanoma cell | | |
| 24 | A431 | Human cutaneous squamous cell carcinoma | | |
| 25 | A673 | Human rhabdomyoma cell | | |
| 26 | PANC-1 | Human pancreatic cancer cell line | | |
| 27 | HCCLM3 | Human high metastatic hepatoma cell | | |
| 28 | A549 | Human non-small cell lung cancer cell | F-12K + 10% FBS | |
| 29 | TT | Human thyroid cancer cell | | |
| 30 | SH-SY5Y | Human neuroblastoma cell | DMEM:F12 1:1 + 10% FBS | |
| 31 | HL-60 | Human leukemic cell line | IMDM + 10% FBS | |
| 32 | SW-480 | Human colorectal cancer cell | L15 + 10% FBS | 37° C. 100% Air |
| 33 | SW 620 | Human colon cancer cell | | |
| 34 | MDA-MB-231 | Human breast cancer cell | | |

1.2.3 Cell Inoculation

After digesting the cells and counting (counting suspended cells directly), the cells were diluted to $1.25 \times 10^5$ cells/ml, inoculated into a 384-well plate (5000 cells/well) with 40 μl per well, centrifuged at 1500 rpm for 1 min, placed into the incubator and incubated overnight.

1.2.4 Cell Administration

The medicaments were diluted in gradient with a 5% glucose solution to 5×, respectively. Each well was dosed with 10 μl medicament, with 4 wells (n=4) for each concentration. The cell viability was measured with Luminescence Cell Viability Assay kit after incubating for 72 hours in an incubator.

According to the molecular weight conversion, the medicament concentration administrated to cells is as follows:

| Concentration setting | mM |
|---|---|
| 1 | 20 |
| 2 | 15 |
| 3 | 10 |
| 4 | 5 |
| 5 | 2.5 |
| 6 | 1.25 |

1.2.5 Detection Method

CellTiter-Glo reagent was added into each well, the volume of which is the same as that of medium. It was shaken on a shaker for 5 min, centrifuged at 1500 rpm for 1 min, and incubated in the dark at room temperature for 15 min. Then the chemiluminescence was detected with BMG PHERAstar.

The cell viability was calculated by using the following formula:

Cell viability (Viability %)=100%×($LUM_{sample\ to\ be\ measured}$−$LUM_{blank}$)/($LUM_{solvent\ control}$−$LUM_{blank}$)

1.2.6 Calculation of $IC_{50}$ of Sample

The curve of Log[concentration] versus cell viability was fitted using Prism 6 to calculate $IC_{50}$ of sample for each cell line.

2. Experimental Results

Figure 2:
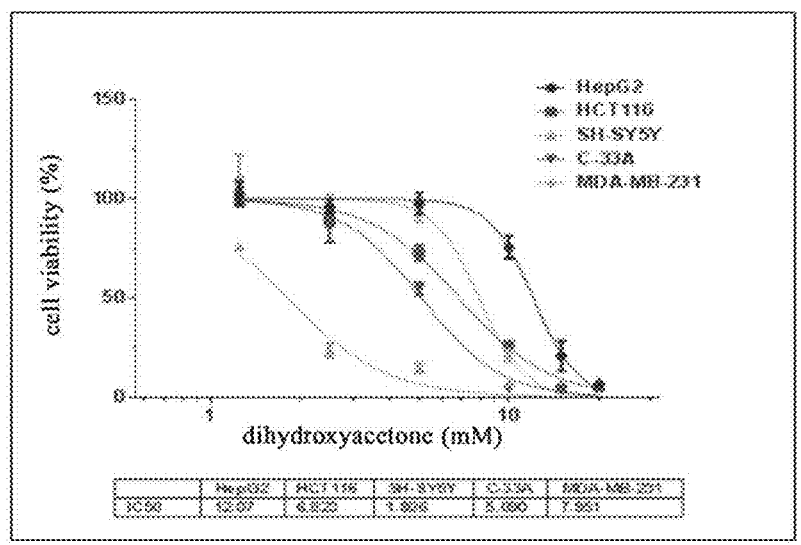
FIG. 2 is the $IC_{50}$ statistical result of dihydroxyacetone for HepG2, HCT116, SH-SY5Y, C-33A, MDA-MB-231 cell lines according to Example 1 of the present invention.

The effects of dihydroxyacetone on cancer cell proliferation were shown in FIGS. 1 and 2, and Table 1.

| No. | Cancer cell line | DDP (μM) | Dihydroxyacetone* (mM) |
|---|---|---|---|
| 1 | HepG2 | 13.90 | 12.07 |
| 2 | HCT116 | 22.86 | 6.82 |
| 3 | SH-SY5Y | 2.89 | 1.81 |
| 4 | C-33A | 2.85 | 5.09 |
| 5 | MDA-MB-231 | N/A | 7.95 |
| 6 | WIL2-S | 9.89 | 12.07 |
| 7 | BEL-7402 | 5.37 | 6.82 |
| 8 | RPMI8226 | 5.79 | 1.81 |
| 9 | SMMC-7721 | 6.19 | 5.09 |
| 10 | SW480 | 16.66 | 7.95 |
| 11 | T24 | 6.22 | 7.67 |
| 12 | A549 | 4.10 | 4.39 |
| 13 | TT | 9.72 | 3.62 |
| 14 | Jurkat | 0.66 | 1.83 |
| 15 | A431 | 9.29 | 5.64 |
| 16 | A375 | 8.25 | 6.18 |
| 17 | A673 | 1.11 | 3.77 |
| 18 | PANC-1 | 22.36 | 7.36 |
| 19 | HCCLM3 | 182.67 | 5.48 |
| 20 | A2780 | 32.16 | 10.61 |
| 21 | DU145 | 4.54 | 7.68 |
| 22 | FaDu | 11.46 | 9.42 |
| 23 | KB | 2.00 | 7.51 |
| 24 | U87MG | 24.03 | 9.21 |
| 25 | Calu-6 | 220.50 | 10.98 |
| 26 | SW620 | 24.43 | 8.54 |
| 27 | Caki-1 | 13.10 | 10.02 |
| 28 | HCC1937 | 14.80 | 10.25 |
| 29 | H460 | 1.67 | 3.79 |
| 30 | HT29 | 48.60 | 4.37 |
| 31 | SGC7901 | 24.03 | 3.74 |
| 32 | S180 | 0.26 | 0.95 |
| 33 | TF1-α | 3.76 | 4.89 |
| 34 | HL-60 | 1.82 | 2.78 |

Notes:
*means that $IC_{50}$ of sample is calculated based on the concentration of dihydroxyacetone; and
N/A means that $IC_{50}$ is not available.

It can be seen from the results that dihydroxyacetone has a relatively broad spectrum effect of anti-proliferation on cancer cells. $IC_{50}$ (half inhibitory concentration) value can be obtained for all of 34 common cancer cell lines involved in the experiments. The results show that dihydroxyacetone has inhibitory effects on common cancers in varying degree, and has significant effects especially on sarcoma, neuroblastoma, myeloma, colon cancer, lung cancer, gastric cancer, leukemia and thyroid cancer and the like.

In summary, the present invention provides a novel use of dihydroxyacetone, which exhibits a relatively high activity against a variety of cancers. In addition, dihydroxyacetone is a safe chemical substance since it has been widely used in human body. Thus, the novel use provided by the present invention allows this substance to expand its application to human body. Therefore, it is expected to be applied in more fields, such as healthcare food, and medicine.

Example 2

Preparation of Tablets

Tablets were prepared according to conventional techniques of pharmaceutics, by using dihydroxyacetone as a pharmaceutically active ingredient and adding pharmaceutical carriers. The preparation method was as follows:

10 mg dihydroxyacetone, 200 mg starch, 100 mg powdered sugar, appropriate amount of magnesium stearate and starch paste as a binder were mixed, granulated, air dried, finished and tableted to obtain tablets.

Example 3

Preparation of Hard Capsules

Hard capsules were prepared according to conventional techniques of pharmaceutics by using dihydroxyacetone as a pharmaceutically active ingredient and adding pharmaceutical carriers. The preparation method was as follows:

10 mg dihydroxyacetone, 200 mg starch, 100 mg powdered sugar, appropriate amount of magnesium stearate and starch paste as a binder were mixed, granulated, air dried, finished and capsulated.

Example 4

Preparation of Soft Capsules

Soft capsules were prepared according to conventional techniques of pharmaceutics by using dihydroxyacetone as a pharmaceutically active ingredient and adding pharmaceutical carriers. The preparation method was as follows:

10 mg dihydroxyacetone, 100 mg soybean oil, and 100 mg polyethylene glycol were filled gelatin as a capsule shell to prepare soft capsules.

Example 5

Preparation of Oral Solution

Oral solution was prepared according to conventional techniques of pharmaceutics by using dihydroxyacetone as a pharmaceutically active ingredient and adding pharmaceutical carriers. The preparation method was as follows:

10 mg dihydroxyacetone, 50 mg glycerin, 100 mg sucrose, appropriate amount of essence were used, and 10 ml water was added.

Example 6

Preparation of Granules

Granules were prepared according to conventional techniques of pharmaceutics by using dihydroxyacetone as a pharmaceutically active ingredient and adding pharmaceutical carriers. The preparation method was as follows:

10 mg dihydroxyacetone, 200 mg dextrin, 100 mg powdered sugar and water as a binder were mixed, granulated, air dried, finished and packaged.

Example 7

Preparation of Pills

Pills were prepared according to conventional techniques of pharmaceutics by using dihydroxyacetone as a pharmaceutically active ingredient and adding pharmaceutical carriers. The preparation method was as follows:

10 mg dihydroxyacetone and 200 mg sodium carboxymethyl cellulose were homogeneously mixed, pilled and dried to obtain 1000 pills, which were film coated.

Example 8

Preparation of Dry Suspensions

Dry suspensions were prepared according to conventional techniques of pharmaceutics by using dihydroxyacetone as a pharmaceutically active ingredient and adding pharmaceutical carriers. The preparation method was as follows:

10 mg dihydroxyacetone, 100 g hydroxypropyl methyl cellulose, 200 g microcrystalline cellulose, and 200 g saccharose were mixed, then 50% ethanol were added to obtain soft material, which were granulated, air dried, finished and packaged.

Example 9

Preparation of Suppositories

Suppositories were prepared according to conventional techniques of pharmaceutics by using dihydroxyacetone as a pharmaceutically active ingredient and adding pharmaceutical carriers. The preparation method was as follows:

600 g cocoa butter as matrix were melted, 10 g dihydroxyacetone were added, mixed homogeneously, injection molded, cooled, scraped and then taken out to obtain suppositories.

Example 10

Preparation of Drip Pills

Drip pills were prepared according to conventional techniques of pharmaceutics by using dihydroxyacetone as a pharmaceutically active ingredient and adding pharmaceutical carriers. The preparation method was as follows:

5 g dihydroxyacetone, 60 g polyethylene glycol 6000

Dihydroxyacetone was added into melted polyethylene glycol 6000, and then mixed at the temperature of 60-90° C. After melting and stirring evenly, the mixture was transferred into a drip tank of a drip pill machine (the temperature was kept at 70-90° C.), dripped into liquid paraffin or methyl silicone oil at 5-17° C. Then, the drip pills were taken out, and the liquid paraffin or methyl silicone oil was removed. The pills were washed and dried to obtain 1000 drip pills.

Example 11

Preparation of Dispersible Tablets

Dispersible tablets were prepared according to conventional techniques of pharmaceutics by using dihydroxyacetone as a pharmaceutically active ingredient and adding pharmaceutical carriers. The preparation method was as follows:

5 g dihydroxyacetone, 18 g lactose, 25 g pregelatinized starch, 35 g microcrystalline cellulose, 7 g low substituted hydroxypropyl cellulose, 6 g polyvinylpyrrolidone, 1 g fine powder silica gel and water as a binder were mixed, granulated, air dried, finished, and then tableted to obtain the dispersible tablets.

Example 12

Preparation of Sugar-Free Granules

Sugar-free granules were prepared according to conventional techniques of pharmaceutics by using dihydroxyacetone as a pharmaceutically active ingredient and adding pharmaceutical carriers. The preparation method was as follows:

10 mg dihydroxyacetone, 4 mg steviosin, and 440 mg dextrin were mixed, and then 95% ethanol was added to prepare soft materials. The soft materials were granulated with 14 mesh, dried at 50-55° C., finished with 12 mesh and subpackaged to obtain the sugar-free granules.

Example 13

1. Experiment Materials 1.1 Test Samples

Name: Dihydroxyacetone (DHA) solid powder

Provided by: Suzhou Yabao Pharmaceutical R&D Co., Ltd.

Positive control: Cisplatin for injection, batch No.: 2WA2A1408055A, manufacturer:

Qilu Pharmaceutical Co., Ltd., specification: 20 mg/bottle 1.2 Test Animals

Species, strains and grades: Balb/c-nude naked mice, SPF grade

Source: Shanghai LingChang Biological Technology Co., Ltd.

License number: SCXK (Shanghai) 2013-00185

Animal certificate number: 2013001812253

Weight: 16-18 g (when arriving)

Gender: Male

2 Test Protocol

Naked mice were subcutaneously inoculated with H460 cells (human large cell lung cancer cell line). When tumors grew to about 100 mm$^3$, 36 naked mice with similar tumor volume and good shape were selected from 70 naked mice, divided into 6 groups with 6 animals in each group;

DHA group: p.o., the volume of administration was 0.1 mL/10 g, bid, three weeks in total;

DHA+Cisplatin group: dihydroxyacetone (DHA): p.o., the volume of administration was 0.1 mL/10 g, bid; Cisplatin: 4 mg/kg, volume of injection was 0.1 mL/10 g, i.p, administration once every 5 days, three weeks in total;

Cisplatin group: 4 mg/kg, volume of injection was 0.1 mL/10 g, i.p, administration once every 5 days, three weeks in total;

Blank group: 0.9% sodium chloride injection, mode of administration was same as DHA group.

3 Experimental Method 3.1 Inoculation 3.1.1 H460 cells were resuscitated and amplified;

3.1.2 After cells were amplified enough, and collected; a cell suspension with a concentration of $2 \times 10^7$ cells/mL was prepared from a 1640 medium without serum;

3.1.3 Naked mice were inoculated subcutaneously at the right side of back, 0.1 mL/mouse, i.e. each naked mouse was inoculated $2 \times 10^6$ cells;

3.1.4 A total of 70 naked mice were inoculated, and tumor growth and tumor size were observed after inoculation.

3.2 Administration by Group 3.2.1 When tumors grew to about 100 mm$^3$, 36 naked mice with similar tumor volume and good shape were selected from 70 naked mice, and divided into 6 groups with 6 animals in each group.

3.2.2 Grouping

Same as "2 Test protocol"

3.3 Preparation of Medicaments

DHA: 15.0 g solid powder was weighed, placed into a 100 mL volumetric flask, added with 5% glucose injection to the scale line, and then shaked while being subjected to ultrasonic to completely dissolve. The mixture was refrigerated at 4° C. when not used. DHA+Cisplatin: 15.0 g solid powder of dihydroxyacetone were weighed, placed into a 100 mL volumetric flask, added with 5% glucose injection to the scale line, and then shaked while being subjected to ultrasonic to completely dissolve. 4 mL of 0.6 mg/mL cisplatin solution were measured and added with 2.0 mL physiological saline to formulate a 0.4 mg/mL (4 mg/kg) cisplatin solution. The solution was refrigerated at 4° C. when not used.

All samples were prepared once every three days.

3.4 Measurement

The tumor volume and body weight were measured three times per week from the first day of administration. Naked mice were sacrificed on $22^{th}$ day. The tumors were taken out, weighed and photographed. The tumor inhibition rate was calculated.

3.5 Evaluation Standard

Changes of tumor volume; changes of animal body weight; final weight of tumor.

4 Detection Index and Calculation Method 4.1 Tumor Volume (TV)

The calculation formula is: TV=½×a×b$^2$, where a and b represents length and width, respectively.

4.2 Relative Tumor Volume (RTV)

The calculation formula is: RTV=TV$_t$/TV$_1$, where TV$_1$ is a tumor volume when being caged and administrated (i.e., d$_1$), TV$_t$ is a tumor volume at each measurement.

4.3 Relative Tumor Proliferation Rate T/C (%)

The calculation formula is:

$$T/C(\%) = \frac{T_{RTV}}{C_{RTV}} \times 100$$

$T_{RTV}$: RTV of treatment group; $C_{RTV}$: RTV of blank control group.

4.4 Tumor Weight Inhibition Rate IR (%)

The calculation formula is:

$$IR(\%) = \frac{C_{TW} - T_{TW}}{C_{TW}} \times 100$$

$T_{TW}$: tumor weight of treatment group; $C_{TW}$: tumor weight of blank control group; TW: tumor weight.

5 Test Results

Figure 3:
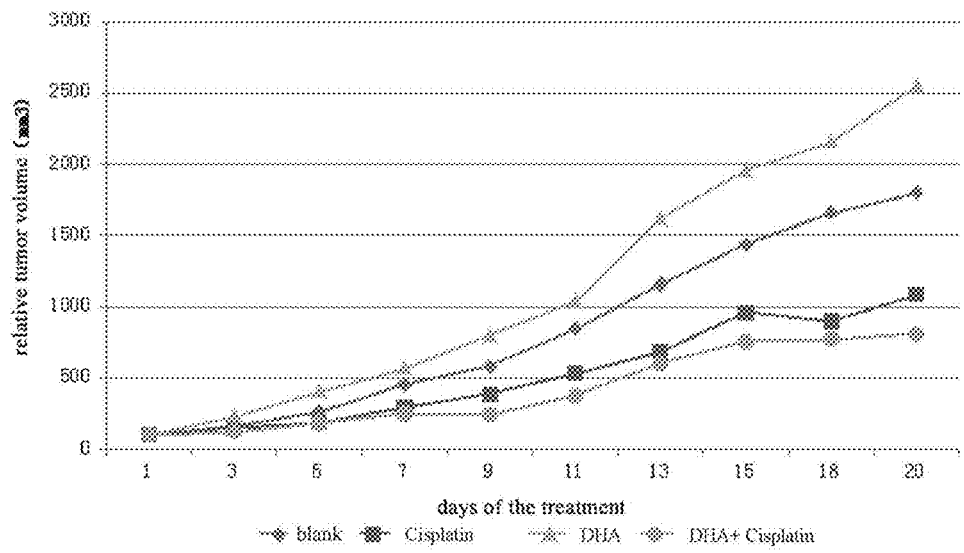
FIG. 3 is a graph showing statistical results of the relative cancer volumes in each group according to Example 13 of the present invention.
Figure 4:
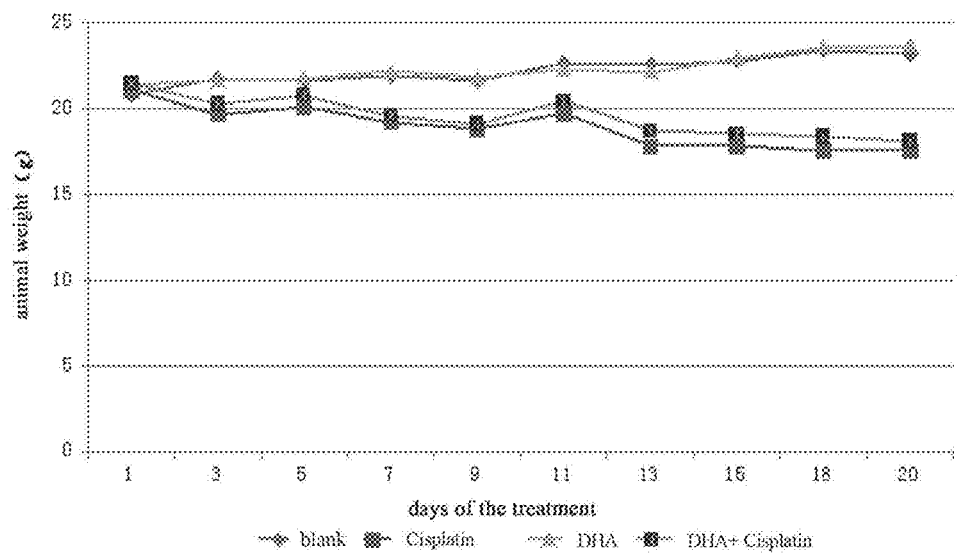
FIG. 4 is a graph showing statistical results of the experimental animal weights in each group according to Example 13 of the present invention.
Figure 5:
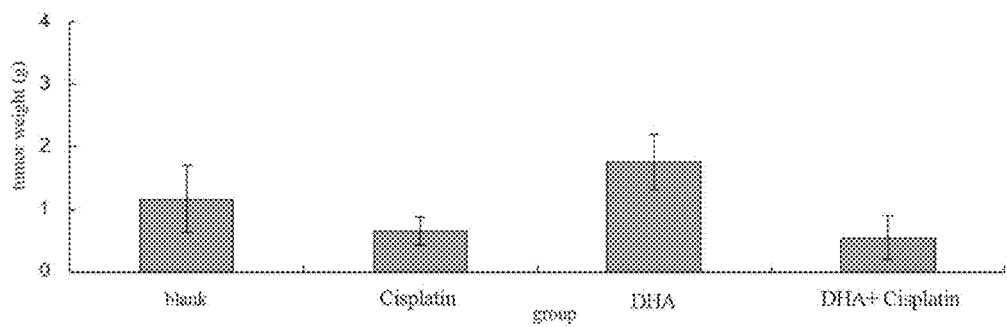
FIG. 5 is a graph showing statistical results of the cancer weights in each group according to Example 13 of the present invention.

The detailed results are shown in Tables 2 and 3 and FIGS. 3, 4 and 5.

TABLE 3

Tumor weight and tumor weight inhibition rate

| Group | Tumor Weight TW (g) | Tumor Weight Inhibition Rate IR (%) |
|---|---|---|
| Blank | 1.17 ± 0.53 | |
| Cisplatin | 0.65 ± 0.23* | 44.6 |
| DHA | 1.76 ± 0.44 | −50.6 |
| DHA + Cisplatin | 0.55 ± 0.13* | 53.3 |

*0.01 < P < 0.05 v.s. Blank.

6 Results and Discussion 6.1 Tumor growth: the results showed that the tumor volume of each group had a relative low dispersion, the standard deviation was less than ¼ of the mean, and the tumors in blank group grew well. RTV=(1797.4±657.6) at the end of the test.

6.2 Body weight: during the whole test, the body weight in groups of Cisplatin and DHA+Cisplatin decreased significantly, and that of the other groups increased normally.

6.3 Cisplatin group: the toxic reaction was very obvious, the body weight decreased significantly, and the body temperature decreased. The body weight decreased about 16.7% at the end of the test, and the animals were in relatively poor condition. Cisplatin was administrated once every 5 days and 4 times in total. The Cisplatin had a significant effect of tumor inhibition (P=0.04), with the final T/C=60.3%, and the tumor weight inhibition rate is 44.6%. This also indicates that this test system is reliable and can be used for the evaluation of pharmaceutical efficacy.

6.4 DHA group: no toxic reaction, this test model did not exhibit a significant effect of tumor inhibition.

6.5 DHA+Cisplatin group: there was toxic reaction, the body weight decreased, the body temperature decreased, and the body weight decreased about 15.7% at the end of the test, which was lower than that of Cisplatin used alone. DHA was administrated twice a day, Cisplatin was administrated once every 5 days and 4 times in total. The effect of tumor inhibition in this group was very significant (P=0.0059), with the final T/C=44.9%, and the tumor weight inhibition rate is 53.3%.

6.6 Summary

In this experiment, DHA+Cisplatin group showed significantly better effects of tumor inhibition in human large cell lung cancer H460 cell transplantation tumor model than Cisplatin group, without increasing the toxicity of chemical

TABLE 2

Number of animals, body weight, tumor volume (TV), relative tumor volume (RTV), relative tumor proliferation rate (T/C)

| Group | Dosage | Number of animals initial | Number of animals final | Body weight (g) D1 | Body weight (g) D20 | TV (mm$^3$) D1 | TV (mm$^3$) D20 | RTV D20 | T/C (%) |
|---|---|---|---|---|---|---|---|---|---|
| Blank | | 6 | 6 | 20.8 ± 1.2 | 23.2 ± 1.1 | 90.14 ± 11.8 | 1596.7 ± 617.1 | 17.9 ± 6.6 | |
| Cisplatin | 4 mg/kg | 6 | 6 | 21.1 ± 0.9 | 17.6 ± 0.7 | 90.30 ± 5.61 | 972.1 ± 289.5 | 10.8 ± 3.3* | 60.3 |
| DHA | | 6 | 6 | 21.4 ± 0.7 | 23.7 ± 1.3 | 90.47 ± 9.91 | 2300.4 ± 585.1 | 25.5 ± 6.2 | 142.0 |
| DHA + Cisplatin | | 6 | 6 | 21.5 ± 1.3 | 18.1 ± 1.8 | 90.41 ± 11.33 | 722.3 ± 189.8 | 8.1 ± 2.3*** | 44.9 |

***P < 0.01 v.s. Blank (RTV)

*0.01 < P < 0.05 v.s. Blank (RTV)

medicament cisplatin. Therefore, DHA is believed to have a better effect of tumor inhibition when combined with chemical medicament Cisplatin.

Example 14

Commercially available dihydroxyacetone (DHA) is white powdery crystals with sweet taste. 300 g of DHA were mixed with 200 g of hydroxypropylmethylcellulose to prepare 40 tablets through a conventional method. Then the tablets were sealed and packaged. 0.0792 g cisplatin and 0.7 g sodium chloride were mixed with 80 ml distilled water, and aseptically packaged into 4 injections. DHA tablets and cisplatin injection were placed into the same package box, packaged into a kit through a conventional method.

Example 15

312 g commercially available dihydroxyacetone (DHA) were equally divided into 40 parts, sealed and packaged into small bags at room temperature in a dry environment. 0.076 g cisplatin were equally divided into 4 parts, sealed and packaged into vials. They were dissolved with glucose for injection when used, respectively. DHA was orally administrated, 0.13 g/kg (calculated with human weight of 60 kg, the same below), twice a day, continuously for 20 days. Cisplatin was intravenously dripped or intramuscularly injected, 0.317 mg/kg, once every 5 days.

Example 16

Figure 6:
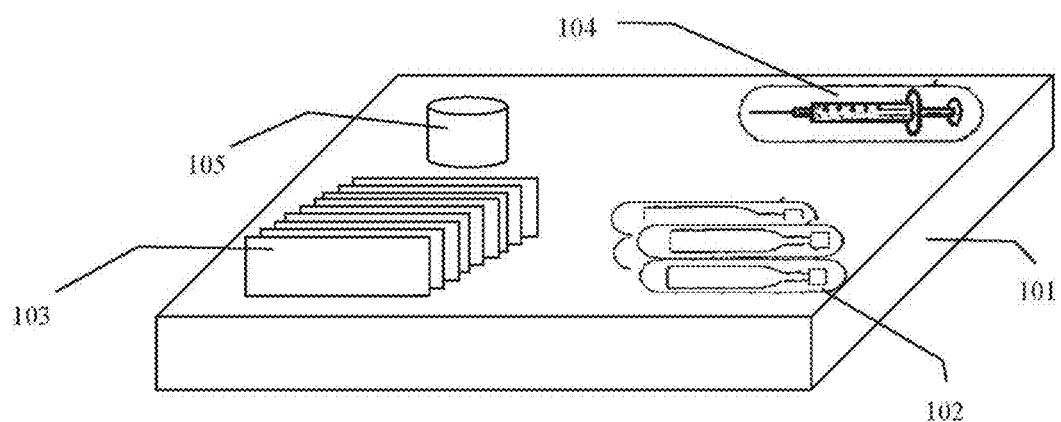
FIG. 6 is a schematic diagram of a kit according to Example 16 of the present invention.

A kit for treating cancer is shown in FIG. 6.

The kit (101) had four vials (102), in which 5 ml cisplatin injection (concentration of 3.98 mg/ml) were sealed and packaged, respectively. There were also 40 sealed bags (103) containing 6.75 g of dihydroxyacetone particles in the kit. The kit was also equipped with a sterile syringe (104) and a medicine cup (105). The dihydroxyacetone particles were placed in the medicine cup (105), dissolved in an appropriate amount of water, and orally administrated after meal, 112.5 mg/kg, twice a day. Cisplatin was injected intramuscularly with a syringe (104), 0.339 mg/kg, once every 5 days.

It needs to be explained that the terms "first" and "second" are only for descriptive purposes and are not to be construed as indicating or imposing a relative importance or indicating implicitly the number of technical features indicated. Thus, a feature that defined by the "first" and the "second" may expressly or implicitly include one or more features. Further, in the description of the present invention, unless otherwise indicated, the meaning of "plural" is two or more.

In the description of this specification, the description of the reference terms "one embodiment", "some embodiments", "illustrative embodiments", "examples", "specific examples", or "some examples" means the combination of specific features, structures, materials, or features described in this embodiment or example is included in at least one embodiment or example of the present invention. In the present specification, the illustrative expression of the above-mentioned terms does not necessarily refer to the same embodiment or example. Moreover, the particular features, structures, materials, or features described may be combined in any one or more embodiment or example in any suitable manner.

While specific embodiments of the present invention have been described in detail, those skilled in the art will appreciate according to all teachings that have been disclosed, various modifications and substitutions can be made to the details, which are within the scope of protection of the present invention. The full scope of the invention is given by the appended claims and any equivalents thereof.

The invention claimed is:

1. A method for treating cancers, wherein the method comprises simultaneously administrating dihydroxyacetone and cisplatin, or administrating a combination of dihydroxyacetone and cisplatin to patients.

2. The method according to claim 1, wherein said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

3. The method according to claim 1, wherein said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

4. A pharmaceutical composition for treating cancer, wherein the composition comprises dihydroxyacetone and cisplatin as active ingredients.

5. The pharmaceutical composition according to claim 4, wherein said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

6. The pharmaceutical composition according to claim 4, wherein said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

7. A pharmaceutical combination for treating cancers, wherein it consists of dihydroxyacetone and cisplatin.

8. The pharmaceutical combination according to claim 7, wherein dihydroxyacetone is in the form of an oral preparation, and cisplatin is in the form of an injection.

9. The pharmaceutical combination according to claim 7, wherein said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

10. The pharmaceutical combination according to claim 7, wherein said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

11. A kit for treating cancers, wherein the kit comprises dihydroxyacetone and cisplatin.

12. The kit according to claim 11, wherein dihydroxyacetone and cisplatin are provided in different containers.

13. The kit according to claim 11, wherein dihydroxyacetone is in the form of an oral preparation, and cisplatin is in the form of an injection.

14. The kit according to claim 11, wherein dihydroxyacetone and cisplatin are provided in a weight ratio of (3375-4125):1.

15. The kit according to claim 11, wherein said cancers comprise at least one selected from the group consisting of nervous system cancer, digestive system cancer, reproductive system cancer, urological cancer, skin cancer, bone cancer, joint system cancer, respiratory system cancer, hematologic cancer and gland cancer.

16. The kit according to claim 11, wherein said cancers comprise at least one selected from the group consisting of neuroblastoma, glioma, colon cancer, rectal cancer, liver cancer, gastric cancer, pancreatic cancer, cervical cancer, breast cancer, ovarian cancer, prostate cancer, bladder cancer, melanoma, epidermal squamous cell carcinoma, rhabdomyoma, multiple myeloma, sarcoma, lung cancer, throat cancer, oral cancer, leukemia, lymphoma and thyroid cancer.

* * * * *